United States Patent [19]

Poisson et al.

[11] Patent Number: 4,879,327

[45] Date of Patent: Nov. 7, 1989

[54] NEW PHOSPHOROUS ACID SALTS, COMPOSITIONS CONTAINING THEM, AND THEIR APPLICATION AS FIREPROOFING AGENTS

[75] Inventors: Pierre Poisson, Bernay; Nadine Rivas, Saint-Ouen du Tilleul; Pierre Deloy, Levallois Perret, all of France

[73] Assignee: Atochem, Paris la Defense, France

[21] Appl. No.: 175,822

[22] Filed: Mar. 31, 1988

[30] Foreign Application Priority Data

Mar. 31, 1987 [FR] France ................................ 87 04488

[51] Int. Cl.$^4$ ............................ C08K 5/51; C07F 9/06; C07F 9/65

[52] U.S. Cl. ........................................ 524/93; 524/100; 524/103; 524/105; 524/139; 544/195; 544/357; 544/410; 546/184; 546/186; 548/266; 548/267; 548/325; 564/457; 564/461; 564/462; 564/510; 564/511; 564/433; 564/434

[58] Field of Search ................... 524/93, 89, 100, 103, 524/105, 139; 260/501.12, 501.14, 501.21, 501.2; 544/195, 357, 410; 548/266, 267, 325

[56] References Cited

U.S. PATENT DOCUMENTS

| | | | |
|---|---|---|---|
| 3,810,850 | 5/1974 | Rowton ................................ | 524/100 |
| 4,008,345 | 2/1977 | Imanaka et al. .................... | 428/272 |
| 4,119,724 | 10/1978 | Thizy et al. ........................... | 424/45 |
| 4,499,222 | 2/1985 | Bernard et al. ...................... | 524/123 |
| 4,574,154 | 3/1986 | Okamoto et al. ................... | 544/198 |
| 4,656,200 | 4/1987 | Clubley et al. ................. | 260/501.21 |

FOREIGN PATENT DOCUMENTS

| | | |
|---|---|---|
| 259232 | 1/1968 | Austria . |
| 0149480 | 1/1985 | European Pat. Off. . |
| 2246586 | 5/1975 | France . |
| 1385781 | 2/1975 | United Kingdom . |

OTHER PUBLICATIONS

CA 68:50570k (1968).
CA 89:111478u (1978).
CA 77:153726f (1972).
CA 70:115256a (1969).
CA 104:6151n (1986).

Primary Examiner—Veronica P. Hoke
Attorney, Agent, or Firm—Sigalos, Levine & Montgomery

[57] ABSTRACT

The invention relates to amine salts of phosphorous acid having a structure of the s-triazine, 1,2,4-triazole, benzimidazole, heptazine, pyrimidine, or piperazine type which may be combined with a polyhydroxylated compound as fireproofing agents for plastics, particularly polyamides and polyolefins, the process of fireproofing said plastics, and the resultant fireproofed plastics.

21 Claims, No Drawings

NEW PHOSPHOROUS ACID SALTS, COMPOSITIONS CONTAINING THEM, AND THEIR APPLICATION AS FIREPROOFING AGENTS

BACKGROUND OF THE INVENTION

The present invention relates to new salts of phosphorous acid. These products can be used as fireproofing agents for plastics.

There are many known phosphorus derivatives, particularly phosphites and phosphonates, which find an application as flame retardants in many flammable materials. U.S. Pat. No. 4,499,222 describes halogenated alkyl phosphonates employed chiefly in polyurethanes.

SUMMARY OF THE INVENTION

New derivatives of phosphorous acid which can be used as flame retardants in plastics have now been found.

More precisely, the present invention relates to new phosphorous acid salts of general formula:

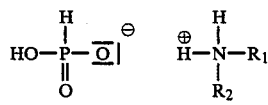
(I)

in which:
- $R_1$ is a hydrogen, an aliphatic hydrocarbon radical containing from 1 to 6 carbon atoms, a cycloaliphatic radical, or a phenyl radical, or said radical being substituted by at least one halogen atom or amino group;
- $R_2$ is an unsubstituted heterocyclic radical or a heterocyclic radical substituted by at least one halogen, amino group, or phenyl, cycloaliphatic, or alkyl radical, or is identical to R; and
- $R_1$ and $R_2$ together from a divalent group consisting of two said radicals connected by an >NH residue, a heteroatom such as —S—, or a methylene residue —CH$_2$—.

The present invention also relates to products of formula (II):

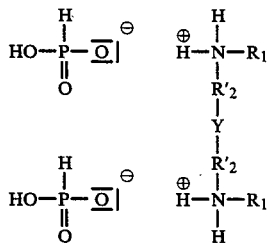
(II)

in which (i) $R_1$ has the same meaning as above or the two radicals $R_1$ together form a divalent radical, (ii) $R'_2$ is an aliphatic, cycloaliphatic, or heterocyclic radical optionally substituted by at least one halogen atom, amino group or phenyl, cycloaliphatic or alkyl radicals, and (iii) Y is a group selected from:

—N—, —NH(CH$_2$)$_n$—NH— with n being from 2 to 6,
 |
 H

—NH(CH$_2$)$_2$—N—(CH$_2$)$_2$—NH, or
 |
 H

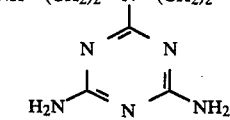

or a single bond.

Two groups of products of formula (I) are advantageously employed.

The invention also comprises compositions thereof and the uses thereof as hereinafter set forth.

DETAILED DESCRIPTION The first group, in which $R_1$ is a hydrogen or an aliphatic radical containing 1 to 2 carbon atoms and $R_2$ is a heterocycle containing nitrogen atoms and capable of being substituted by amino groups, halogens, aliphatic radicals containing up to 10 carbon atoms or phenyl radicals. In this first group, preference is given to the products in which $R_1$ is a hydrogen and $R_2$ is one of the following heterocycles:

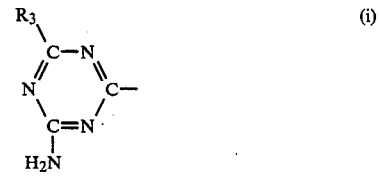
(i)

(s-triazine structure)

in which $R_3$ may be an amino radical, an aliphatic hydrocarbon radical containing from 1 to 10 carbon atoms, or a phenyl radical, substituted or otherwise.

(ii)

(1,2,4-triazolyl structure) and its isomers in which $R_4$ may be a hydrogen or an amino radical.

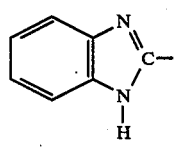
(iii)

(benzimidazolyl structure)

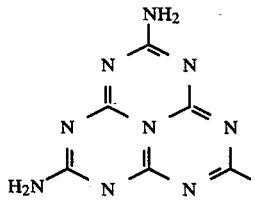
(iv)

(heptazine structure)

-continued (v) [1,3-diazine or pyrimidine structure]

In this first group, use is made more particularly of:
(i) melamine phosphite:

(i) melamine phosphite:

(ii) melem phosphite:

(iii) benzoguanamine phosphite:

(iv) acetoguanamine phosphite:

(v) 3-amino-1,2,4-triazole phosphite:

(vi) 4-amino-1,2,4-triazole phosphite:

-continued (vii) guanazole phosphite:

or (viii) benzimidazole phosphite:

The second group in which $R_1$ is an aliphatic radical containing up to 4 carbon atoms capable of being substituted by halogens or amino groups, $R_2$ is identical with $R_1$, and $R_1$ and $R_2$ together form a divalent group connected by an >NH residue, a methylene residue, or a heteroatom.

In this second group, preference is given to the radicals $R_1$ and $R_2$ such that a piperazine or piperidine structure is present In this second group, use is made more particularly of:

(i) piperazine phosphite:

or (ii) piperidine phosphite:

Among the products of formula (II) use is advantageously made of those in which $R_1$ is a hydrogen or an aliphatic radical containing 1 to 2 carbon atoms and $R'_2$ a heterocycle containing nitrogen atoms and capable of being substituted by amino groups, halogens, and aliphatic radicals containing up to 10 carbon atoms. Preference is given to the products in which $R_1$ is a hydrogen and $R'_2$ a triazine structure such as:

Among the products of formula (II) it is also advantageously possible to employ those in which the two radicals $R_1$ together form a divalent group consisting of aliphatic residues containing 1 to 2 carbon atoms linked by a single bond, and Y is a single bond.

Use is made more particularly of:

melam diphosphite:

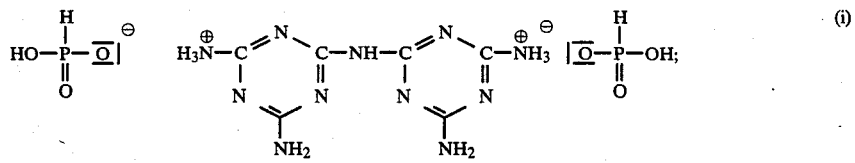

ethylenedimelamine diphosphite:

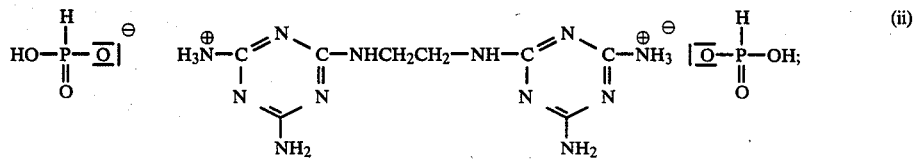

diethylenetrimelamine diphosphite:

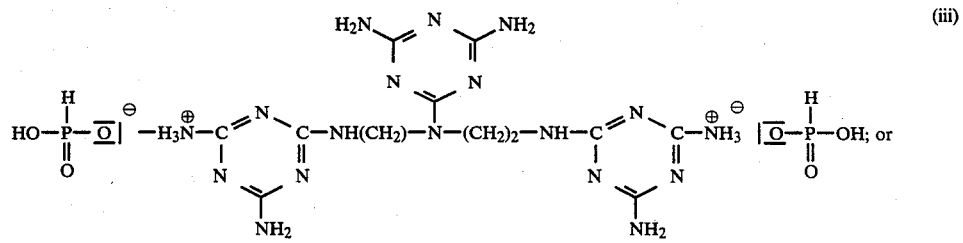

piperazine diphosphite:

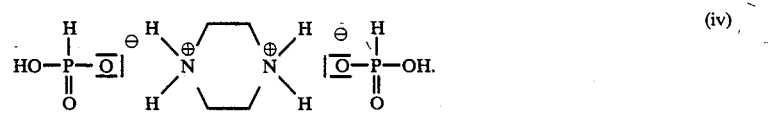

The compounds of the present invention may be obtained by various means.

A compound of structure

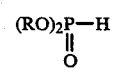

in which R may be $CH_3$ or $CH_3CH_2-$, may be reacted together with a compound of general formula:

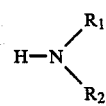

$R_1$ and $R_2$ having the same meanings as above, and water. This process is long and not very economical. It has been found that it was preferable to react phosphorous acid (in the form of aqueous solution) in an aqueous medium with a compound of structure:

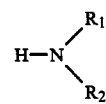

according to the reaction:

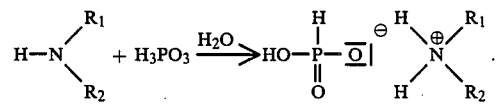

Advantageously, the molar ratio phosphorous acid/amine is from 0.9:1 to 1.1:1, but preferably about 1:1.

Among the amines which may be employed according to the invention, there may be mentioned, for example, melamine, benzoguanamine, acetoguanamine, 2,4-diamino-6-nonyl-1,3,5-triazine, 3-amino-1,2,4-triazole, guanazole, melam, melem, piperazine, 2-aminobenzimidazole and N,N'-bis(1,3,5-triazinyl-2,4,6-triamino)-1,2-ethane.

A preferred method for preparing amine phosphites according to the invention consists of treating an aqueous amine suspension with an aqueous solution of phosphorous acid at a concentration of between 60 and 80%, preferably in the region of 70% by weight The reaction may be carried out between 20° and 100° C., preferably at about 30° to 50° C., for a period which may range from one to several hours with good stirring. The amine phosphites obtained in this manner are insoluble or poorly soluble in the reaction medium. The filtrate may advantageously be reemployed for a subsequent operation, and this allows the yield to be improved.

Known means are used to isolate the compounds; such as filtration, washing of the cake obtained, and drying at about 100° C. under reduced pressure.

Advantageously, the product is ground to produce powders of a suitable particle size to allow satisfactory dispersion in the polymeric matrix to be fireproofed. Advantageously, the particle size is between 1 and 50 microns and preferably between 5 and 25 microns.

The products are characterized by elemental analysis, infrared, and proton, carbon 13 and phosphorus 31 NMR.

The purity may be rapidly determined simply by acidimetry.

Amine phosphites are products which are stable at temperatures below 250° C. The amine phosphites obtained in this manner may be employed as fireproofing agents for organic materials and especially for plastics.

The present invention also relates to the application of the products of the present invention as fireproofing agents, as well as the use of morpholine phosphite, cyclohexylamine phosphite, and aniline phosphites.

Advantageously, these products are employed for fireproofing polyamides and polyolefins.

"Polyamides" are intended by us to mean the polymers resulting from the polycondensation of one or more aminoacids such as aminocaproic, 7-aminoheptanoic, 11-aminoundecanoic acids, and the like; of one or more lactams such as caprolactam, lauryllactam, and the like; of one or more salts or mixtures of diamines such as hexamethylenediamine or dodecamethylenediamine with diacids such as terephthalic, adipic or azelaic acids, and the like; or of mixtures of all these monomers, resulting in copolyamides.

The amine phosphites of the present invention are advantageously employed in a proportion of 1 to 20% by weight relative to the fireproofed polyamide and, preferably, in a proportion of 3 to 12%.

"Polyolefins" is intended by us to mean all the polymers of monoolefins which correspond to the formula $CH_2=CH-A$ in which A denotes a hydrogen, a substituted or unsubstituted hydrocarbon radical containing 1 to 2 carbon atoms, a phenyl radical or an acetoxy radical.

Polymers of this kind which can be fireproofed according to the invention are polyethylenes, ethylene-propylene copolymers, polypropylene and poly(vinyl acetate).

The amine phosphites of the present invention are advantageously employed in a proportion from 10 to 60% by weight relative to the fireproofed polyolefins, and preferably in a proportion of 25 to 35%.

According to a preferred application of the products of the invention, they are employed in intumescent systems.

An intumescent system is characterized by the fact that at the time of the combustion the compounds of the said system interreact to form a noncombustible, more or less cellular, carbonaceous foam which retards the release of flammable gases released from the heated mass. Such systems generally consist of three main constituents:

(a) a foamer which produces nonflammable gases or vapors which assist in the formation of the foam. These are generally nitrogen compounds such as urea, guanidine, melamine, and the like;

(b) a carbonization agent which contributes to the formation of carbonaceous materials ("chars"). These are generally polyhydroxy compounds such as sugars, mono-, di- or tripentaerythrite, trimethylolpropane, and the like; and (c) a catalyst which is generally an acidic compound or, more precisely, a compound which generates acid at the time of the combustion. This is to say that this acid is in most cases in a combined form. The most widely employed catalysts are ammonium polyphosphates, melamine phosphates, melamine borates and melamine sulphates. As can be seen, the majority of combinations contain both the foamer and the acid in a combined form.

The amine phosphites of the present invention may also act both as a foamer as a result of the presence of the nitrogen compound and as a catalyst, as a result of the presence of combined phosphorous acid.

Compared with the abovementioned combinations, they offer the advantage of being well-defined combinations, slightly or nonhygroscopic, easy to obtain from inexpensive reactants, and of being more reducing in character than the derivatives of phosphorous acids, resulting in a very high efficiency during the combustion.

The amine phosphites of the present invention, combined with polyhydroxylated compounds produce very efficient intumescent systems which make it possible to improve the behavior towards fire of plastics especially of polyolefins and polyamides, the said polyamides and polyolefins having been defined earlier.

The polyhydroxy compounds which may be suitable are erythritol, sorbitol, mannitol, dianhydrosorbitol, anhydroerythritol and mono-, di- or tripentaerythrite. Preference is given to the use of monopentaerythrite, which is called "pentaerythritol" hereinafter.

All the amine phosphites of the present invention may be employed as amine phosphites, but melamine phosphite is preferably employed.

Where polyamides are involved, a variable percentage of one or more polyhydroxylated compounds, of between 0.2 and 10% by weight relative to the fireproofed polyamides, and preferably between 1 and 3%, is added in addition to the amine phosphites of the invention.

Where polyolefins are involved, the proportions of the constituents defined by the molar ration R = amine phosphite/polyhydroxy compound may be between 1:1 to 7:1, preferably 2 1 to 4:1.

As in the case of the polyamides, the polyhydroxylated compound may be one or more products.

The quantity of the constituents; amine phosphite plus polyhydroxylated compound, defined as the proportion of fillers, is a function of the desired degree of fireproofing. It may be between 20 and 60% by weight relative to the fireproofed resin. As a general rule, improved behavior towards fire and good retention of the mechanical properties are obtained with a proportion of fillers between 25 and 35%. The incorporation of the amine phosphites and of the polyhydroxylated compound is carried out by kneading both these compounds, finely divided, into the molten polymer. Any conventional kneading apparatus providing good dispersion can therefore be suitable with kneaders of the Buss type being particularly suitable for this purpose.

The extrusion conditions must be suitable in order to produce good dispersion of the additives.

The compound obtained is granulated and the granules obtained are injection- or compression-molded at suitable temperatures into standard test specimens for carrying out the UL 94 fire reaction test according to the NF Standard T51072 and for measuring the oxygen index according to NF Standard T51071.

A simple operating procedure consists in dry mixing the polymer granulate, the amine phosphite and the polyhydroxylated compound in a mixer of the Turbula type or more simply in a drum and in feeding this mixture into an appropriate kneader.

Polymer-amine phosphite masterbatches may also be prepared. Using this compound in a granulated form, a mixture with the polyhydroxylated compound may be produced as before in a mixer of the Turbula type and fed into a kneader. It is also possible to feed an extruder at the head of a compounding screw with a polymer-amine phosphite mixture, and then to introduce the polyhydroxylated compound in the middle of the screw by means of a metering device of the Soder type.

The invention will be further described in connection with the following examples which are set forth for purposes of illustration only.

EXAMPLE 1

Melamine phosphite

The following are introduced into a 250-ml reactor equipped with a stirrer, a temperature sensor and a reflux condenser:
(i) 12.6 g of melamine (0.1 mole),
(ii) 50 ml of diethyl phosphite, and
(iii) 10 g of water,
and then the whole is heated on a boiling water bath with good stirring.

During the first hour's heating, a white slurry is obtained, which becomes increasingly clearer or even transparent. Heating of the solution obtained in this manner is continued and the formation of a precipitate and a slight foaming are observed. A considerable reflux is produced. After 2 hours' heating, a distillation head is fitted and a product with a boiling point of 78° C. is recovered. The reaction is stopped when no more product distills over.

After filtration while hot, the cake is drained and washed with ether. The drained product is dried under vacuum.

18 g of melamine phosphite are obtained.

Yield: 86.5%, expressed relative to the melamine employed.

Elemental analysis
$C_3H_9N_6PO_3$

|  | C | H | N | P |
|---|---|---|---|---|
| % calculated | 17.3 | 4.32 | 40.38 | 14.90 |
| % found | 17.3 | 4.6 | 39.94 | 13.31 |

Infrared spectrum
$\nu P{-}H = 2400$ cm$^{-1}$
$\nu P{-}OH = 2700$ cm$^{-1}$
$\nu C{=}N$ (ring) $= 1620$ cm$^{-1}$, 1520 cm$^{-1}$
$\nu NH_3\oplus = 3140$ cm$^{-1}$
$\nu NH_2 = 3420$ cm$^{-1}$
$\delta NH_3\oplus =$  cm$^{-1}$
Proton NMR spectrum (deuterated DMSO solvent)
(d) H₂N

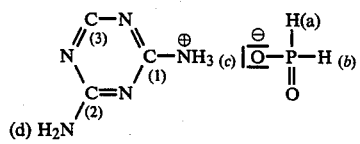

(d) H₂N $\delta = 10.1$ ppm (s) 1 Ha
$\delta = 6.75$ ppm (d) 1 Hb JP—H$_{(b)} = 600$ Hz
$\delta = 7.47$ ppm (s) 3 H$_{(c)}$ + 4H$_{(d)}$
$^{13}$C NMR spectrum (deuterated DMSO solvent)

-continued $\delta = 162.1$ ppm C1 + C2 + C3
$^{31}$P NMR spectrum (deuterated DMSO solvent)
$\delta = 5.7$ ppm
Thermal stability: P = 2.98% at 250° C.

EXAMPLE 2

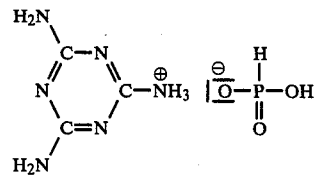

1 liter of distilled water and 126 g of melamine (1 mole) are introduced into a 2-1 reactor equipped with a stirrer, a temperature sensor, a dropping funnel and a reflux condenser. Vigorous stirring is applied so as to disperse the melamine, and then 117.15 g of an aqueous solution containing 70% phosphorous acid (82 g $H_3PO_3$: 1 mole) is added over 30 minutes. When the addition is completed, the reaction mixture is kept well stirred at ambient temperature for 3 hours.

The product is filtered off, washed and dried under reduced pressure at 100°-120° C. 171 g of melamine phosphite are obtained. Yield: 82%

| Elemental analysis $C_3H_9N_6PO_3$ | | | | |
|---|---|---|---|---|
|  | C | H | N | P |
| % calculated | 17.3 | 4.32 | 40.38 | 14.90 |
| % found | 17.7 | 4.23 | 40.76 | 14.02 |

Infrared spectrum

| $\nu P{-}H$ | = 2356 cm$^{-1}$ |
|---|---|
| $\nu P{-}OH$ | = 2700 cm$^{-1}$ |
| $\nu NH_3\oplus$ | = 3125 cm$^{-1}$ |
| $\nu P{=}O$ | = 1078 cm$^{-1}$ |

Proton NMR spectrum (deuterated DMSO solvent)

$\delta = 6.62$ ppm P—H JP-H = 612 Hz $^{13}$C NMR spectrum (deuterated DMSO solvent)

$\delta = 162.1$ ppm 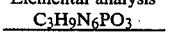

EXAMPLE 3

Preparation of melamine phosphite using a procedure similar to Example 2 except that the quality of water is halved: 500 ml for 1 mole of melamine.

| Elemental analysis $C_3H_9N_6PO_3$ | | | | |
|---|---|---|---|---|
|  | C | H | N | P |
| % calculated | 17.3 | 4.32 | 40.38 | 14.90 |
| % found | 17.13 | 4.29 | 40.12 | 14.66 |

Infrared spectrum $\nu P{-}H = 2400$ cm$^{-1}$ $^{13}$C NMR spectrum (deuterated DMSO solvent)

$\delta = 162.33$ ppm

Proton NMR spectrum (deuterated DMSO solvent)

$\delta = 9.76$ ppm P—O—H
$\delta = 6.75$ ppm P—H JP—H = 600 Hz 

δ = 7.49 ppm NH$_2$, NH$_3^⊕$

EXAMPLE 4

Benzoguanamine phosphite 93.6 g of benzoguanamine (0.5 mole) in 600 ml of water are introduced into a 2-l reactor equipped as in Example 2 and efficient stirring is applied to obtain good dispersion and 62.2 g of an aqueous solution of H$_3$PO$_3$ at a concentration of 72.5% (0.55 mole 100% H$_3$PO$_3$) are introduced. When the addition is completed, the mixture is heated to 70° C. for 1 hour and 30 minutes. It is cooled and filtered. The cake is slurried twice with 300 ml of water, is drained and is dried at 80° C. under reduced pressure, to constant weight.

127 g of benzoguanamine phosphite are obtained. Yield 94.3%

| Elemental analysis C$_9$H$_{12}$N$_5$PO$_3$ | | | | |
|---|---|---|---|---|
| | C | H | N | P |
| % calculated | 40.14 | 4.46 | 26.02 | 11.52 |
| % found | 40.35 | 4.52 | 26.15 | 11.3 |

Infrared spectrum
υP—H = 2300 cm$^{-1}$
υP—OH = 2700–2800 cm$^{-1}$
υCH$_{ar}$ = 3060 cm$^{-1}$
υNH$_3^⊕$ = 3160 cm$^{-1}$
υNH$_2$ = 3380 cm$^{-1}$
Proton NMR spectrum (deuterated DMSO solvent)
δ = 6.67 ppm P—H JP—H = 631 Hz
$^{13}$C NMR spectrum (deuterated DMSO solvent)

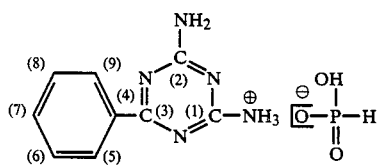

δ = 166.75 ppm C$_1$–C$_2$
δ = 169.76 ppm C$_3$
δ = 136.46 ppm C$_4$
δ = 128.76 ppm C$_5$–C$_9$
δ = 127.93 ppm C$_6$–C$_8$
δ = 131.43 ppm C$_7$

EXAMPLE 5

Guanazole phosphite 500 ml of water and 599.3 g of guanazole (6.05 moles) are introduced into an apparatus identical with that of Example 2. The suspension is stirred and 720 g of a 69% strength aqueous solution of H$_3$PO$_3$ (6.05 moles) are introduced at ambient temperature.

During the addition, which takes 70 minutes, the mixture passes through a homogeneous stage and the temperature rises from 20 to 35° C.

Crystallization is seen to begin at the end of the addition. The mixture is then kept well stirred for 1 hour and 30 minutes at 30°–35° C. It is then cooled to about 10° C. and the crystals produced are filtered off. They are washed with the minimum quantity of cold water and are dried under vacuum at 140° C.

853 g of guanazole phosphite are obtained, in the form of white crystals which melt at 163.2° C.

| Elemental analysis | | | |
|---|---|---|---|
| | C | H | N |
| % calculated | 13.25 | 4.41 | 38.67 |
| % found | 12.6 | 4.38 | 38.22 |

Infrared spectrum
υP—H = 2200 cm$^{-1}$
υP—OH = 2680 cm$^{-1}$
υNH$_2$, NH$_3^⊕$ = 3080 cm$^{-1}$, 3160 cm$^{-1}$, 3360 cm$^{-1}$
Proton NMR spectrum (deuterated DMSO solvent)
δ = 6.65 ppm P—H JP—H = 619 Hz
$^{13}$C NMR spectrum (deuterated DMSO solvent)

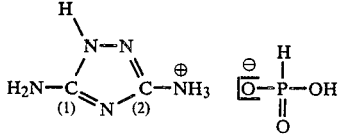

δ = 153.4 ppm C$_1$, C$_2$

EXAMPLE 6

3-Amino-1,2,4-triazole phosphite 250 g of water and 464 g of 3-amino-1,2,4-triazole (5.52 moles) are introduced into an apparatus identical with that of Example 2. The suspension is stirred and 624.5 g of a 72.5% strength aqueous solution of H$_3$PO$_3$ (5.52 moles of H$_3$PO$_3$) are introduced dropwise.

The addition takes place at ambient temperature, the temperature rises to 30° C. When the addition is completed (4 hours and 30 minutes), the suspension is kept well stirred for 1 hour and 30 minutes at about 35° C. and is then filtered, and the cake obtained is drained and dried at 100° C. under reduced pressure. 914 g of 3-amino-1,2,4-triazole phosphite are obtained.

Yield: 84%
Melting point: 130.9° C.

| Elemental analysis C$_2$H$_7$N$_4$O$_3$P | | | | |
|---|---|---|---|---|
| | C | H | N | P |
| % calculated | 14.45 | 4.21 | 33.73 | 18.67 |
| % found | 13.89 | 4.32 | 32.91 | 17.85 |

Infrared spectrum
υP—H = 2410 cm$^{-1}$
υP—OH = 2680 cm$^{-1}$
υNH$_3^⊕$, NH$_2$ = 3140 cm$^{-1}$, 3280 cm$^{-1}$
υP=O = 1105 cm$^{-1}$
Proton and $^{13}$C NMR spectrum

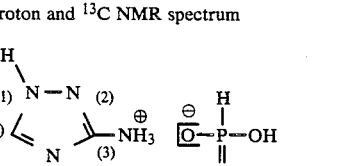

$^{31}$P NMR spectrum (D$_2$O solvent H$_3$PO$_4$ reference)
δ = 5.14 ppm
Proton NMR spectrum (deuterated DMSO solvent)
δ = 6.88 ppm P—H JP—H = 614 Hz
$^{13}$C NMR spectrum (deuterated DMSO solvent)
δ = 140.73 ppm C$_5$
δ = 152.76 ppm C$_3$

EXAMPLE 7

Acetoguanamine phosphite 2 liters of water and 125 g of acetoguanamine (1 mole) are introduced into a 4-l reactor equipped with a stirrer, a temperature sensor and a reflux condenser. Stirring is applied and 117.7 g of a 69.7% strength aqueous solution of H3PO3 are then introduced dropwise.

When the addition is completed the reaction mixture is heated for 1 hour to 50° C. and is then cooled, filtered and drained. The product is washed and is then dried under reduced pressure at about 100° C.

|  | Elemental analysis $C_4H_{10}N_5O_3P$ | | |
|---|---|---|---|
|  | C | H | N |
| % calculated | 23.18 | 4.83 | 33.81 |
| % found | 23.28 | 4.75 | 33.64 |
| Infrared spectrum | | | |
| $\nu P\text{—}H = 2400$ cm$^{-1}$ | | | |
| $\nu C=N = 1670$ cm$^{-1}$ | | | |
| $^{13}C$ carbon NMR spectrum (deuterated DMSO solvent) | | | |

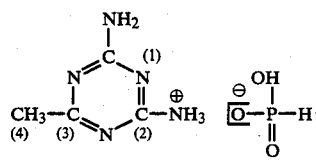

$\delta = 22.85$ ppm $C_4$
$\delta = 164.67$ ppm $C_1, C_2$
$\delta = 171.56$ ppm $C_3$

EXAMPLE 8

Piperazine phosphite

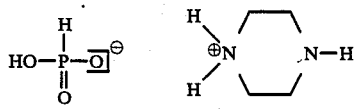

86 g of piperazine (1 mole) in 500 ml of water are introduced into a 2-liter reactor equipped as in Example 2. The solution is stirred and 116.7 g of an aqueous solution of H3PO3 at a concentration of 70.25% are introduced dropwise over 40 minutes. The temperature rises from 25° C. to about 40° C. at the end of addition. After cooling, the solution obtained is partially concentrated under reduced pressure.

The precipitate obtained is filtered off and drained and then dried at 100° C. under reduced pressure.

127 g of piperazine phosphite are obtained.
Melting point: 215° C.

| Infrared spectrum |
|---|
| $\nu = PH = 2320$ cm$^{-1}$ |
| $\delta NH_2 \oplus = 1440$ cm$^{-1}$ |
| Proton NMR spectrum (D$_2$O solvent) |
| $\delta = 6.78$ ppm (d) P—H JP—H = 582 Hz |
| $\delta = 3.34$ ppm (s) —CH$_2$— (8 protons) |
| $^{13}C$ NMR spectrum (D$_2$O solvent) |
| $\delta = 43.416$ ppm |

EXAMPLE 9

Piperazine diphosphite

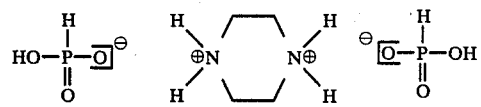

86 g of piperazine (1 mole) in 250 ml of water are introduced into a 2-liter reactor equipped as in Example 2. Stirring is applied and then 233.5 g of an aqueous solution of H3PO3 at a concentration of 70.25% (2 moles of 100% H3PO3) are introduced dropwise over 1 hour and 30 minutes. The temperature rises to approximately 45°-50° C. Stirring is continued for 1 hour and then, after cooling, the solution is concentrated to dryness under reduced pressure, and the product is then dried at 100° C. Piperazine diphosphite is obtained.

Melting point 138° C.

| Infrared spectrum | |
|---|---|
| $\nu P\text{—}H =$ | 2360 cm$^{-1}$ |
| $\delta NH_2\oplus =$ | 1450 cm$^{-1}$ |
| Proton NMR spectrum (D$_2$O solvent) | |
| $\delta = 6.85$ ppm (d) P—H JP—H = 627 Hz | |
| $\delta = 3.57$ ppm (s) —CH$_2$— (8 protons) | |
| $^{13}C$ NMR spectrum (D$_2$O solvent) | |
| $\delta = 42.82$ ppm | |

The efficiency of the amine phosphites employed by themselves or combined with pentaerythritol, as agents improving the behavior of polyamides and of polyolefins towards fire has been tested according to the following examples:

EXAMPLE 10 (control)

Granules of BMNO grade polyamide 11 marketed by the applicant company and having the following characteristics: =1.01, relative density =1.03, and melting point =185° C., are extruded on a Buss kneader.

The granules obtained are injection-molded at a temperature of 230° C. into test specimens on which the UL 94 test and the 0I oxygen index measurements are carried out.

EXAMPLE 11

The following are blended dry in a drum:
(i) 9,700 g of type BMNO polyamide 11 granules having the same characteristics as in Example 10, and
(ii) 300 g of melamine phosphite.

This mix is fed to a Buss Ko-Kneader model PR 46, in which the average temperature is 205°-210° C. The rods which are extruded from it are cooled and chopped. The granules obtained in this manner are dried and then injection-molded at a temperature of about 225° C.

The UL 94 test and the oxygen index measurement are carried out on these test specimens.

EXAMPLES 12, 13 AND 14

These are similar to Example 11, but with different proportions of melamine phosphite.

EXAMPLE 15

The following are blended dry in a drum:
(i) 9,200 g of polyamide 11 (BMNO grade) granules,
(ii) 750 g of melamine phosphite, and
(iii) 50 g of pentaerythritol (tech. grade crystals marketed by Celanese Chemical Company) The subsequent procedure is as in Example 11.

EXAMPLES 16, 17, 18, 19, AND 20

These are similar to Example 15, but with different proportions of melamine phosphite and pentaerythritol.

EXAMPLE 21

Similar to Example 10 except that melamine phosphite is replaced by benzoguanamine phosphite.

EXAMPLE 22

The following are blended dry in a drum:
(i) 8,900 g of polyamide 11 (BMNO grade) granules,
(ii) 800 g of guanazole phosphite, and
(iii) 300 g of pentaerythritol.
The subsequent procedure is as in Example 11.

EXAMPLE 23 (control)

A polyamide 12 is prepared by introducing into a stainless steel autoclave:
(i) 30 kg of lauryllactam,
(ii) 3 kg of water, and
(iii) 255 g of dodecanedioic acid.
The temperature is raised to 280° C. at an elevated pressure of 25 to 30 bars, which is maintained for 2 hours. The pressure is released while the temperature is kept at 250° C. and the polymerization is continued at atmospheric pressure and under a gentle stream of nitrogen for the time required to obtain a polymer with an inherent viscosity of 1.01, which is extruded out of the autoclave (using nitrogen pressure) in the form of rods which are solidified by cooling in water. These rods are then chopped into granules, which are dried. The granules obtained in this manner are injection-molded as described in Example 10.

EXAMPLE 24

The following are blended dry in a drum:
(i) 8,200 g of polyamide 12 granules obtained in Example 23,
(ii) 1,500 g of melamine phosphite, and
(iii) 300 g of pentaerythritol. The subsequent procedure is as in Example 11.

EXAMPLE 25

Similar to Example 24 except that melamine phosphite is replaced by 3-amino-1,2,4-triazole phosphite.

EXAMPLE 26

The following are blended dry in a drum:
(i) 8,950 g of a grade RMN CD polyamide 6 marketed by the applicant company under the name of Orgater,
(ii) 1,000 g of melamine phosphite, and
(iii) 50 g of Irganox 1098 [N,N'-bis(3,5-di-tert-butyl-4hydroxy-phenylpropionyl)hexamethylenediamine].
This mix is fed into a Buss kneader, model PR 40/70, in which the average temperatures are within 230°–235° C. The rods are cooled and granulated.
The granules are dried and then injection-molded at a temperature of 250°–260° C. into standardized test specimens in order to carry out the UL 94 test and to measure the OI oxygen index.

The results obtained are given in Table I below. These examples show, in fact, that the amine phosphites by themselves; and better when combined with pentaerythritol, improve the behavior of polyamides towards fire.

The examples which follow demonstrate the efficiency of the amine phosphites-pentaerythritol intumescent system for improving the behavior of polyolefins, especially polypropylene, towards fire.

EXAMPLE 27

Standardized test specimens are compression-molded on a Minimatic press from a PK 1060P polypropylene powder marketed by Hoechst, in order to carry out the UL 94 test and the measurement of oxygen index.

EXAMPLE 28

The following are blended dry in a drum:
(i) 5,450 g of PK 1060P polypropylene powder,
(ii) 3,500 g of melamine phosphite, and
(iii) 1,050 g of pentaerythritol.
A Buss kneader, model PR 46, in which the average temperature is 175° C., is fed. The rods which are extruded from it are cooled and chopped into granules which are compression-molded on a Minimatic press at a temperature in the region of 190° C.

EXAMPLES 29, 30, 31 AND 32

These are similar to Example 28, but the proportions of melamine phosphite and of pentaerythritol are different as shown in Table II below. The extrusion has been carried out on a Collin model ZK 50 extruder at an average temperature of 170°–180° C.

EXAMPLE 33

Similar to Example 30, except that melamine phosphite is replaced by acetoguanamine phosphite.

EXAMPLE 34

Type 3050 MN1 polypropylene granules marketed by the applicant company are extruded on a Buss kneader, model PR 40/70.
The granules obtained are injection-molded into standardized test specimens on which the UL 94 test and the measurement of the oxygen index are carried out.

EXAMPLE 35

The following are blended dry in a drum:
(i) 6,000 g of 3050 MN1 polypropylene granules, and
(ii) 3,000 g of melamine phosphite.
This mix is fed to a Buss kneader, model PR 40/70, at the head of the compounding screw, and the pentaerythritol powder (1,000 g) is introduced by means of a Soder metering device in the middle of the kneading screw at a rate such that a percentage of 10% (by weight) is present in the final composition. The subsequent procedure is as in Example 27.

EXAMPLE 36

Similar to Example 35, except that the percentages of melamine phosphite and of pentaerythritol are different as shown in Table II below.
The results obtained are given in Table II.
These examples demonstrate well the efficiency of the amine phosphites in the intumescent system for improving the behavior of polypropylene towards fire.

The formation of a "meringue" which acts as an insulator, delaying the release of flammable gases by the heated mass, is observed, in fact, during the fire tests.

TABLE I

| Formulation | \multicolumn{17}{c}{Examples} |
|---|---|---|---|---|---|---|---|---|---|---|---|---|---|---|---|---|---|
| | 10 | 11 | 12 | 13 | 14 | 15 | 16 | 17 | 18 | 19 | 20 | 21 | 22 | 23 | 24 | 25 | 26 |
| Polyamide 11 | 100 | 97 | 92.5 | 90 | 87.5 | 92 | 91.5 | 91 | 90 | 87.8 | 88 | 88 | 89 | | | | |
| Polyamide 12 | | | | | | | | | | | | | | 100 | 82 | 82 | |
| Polyamide 6 | | | | | | | | | | | | | | | | | 89.5 |
| Melamine phosphite | | 3 | 7.5 | 10 | 12.5 | 7.5 | 7.5 | 7.5 | 7.5 | 9.2 | 10 | | | | 15 | | 10 |
| Guanazole phosphite | | | | | | | | | | | | | 8 | | | | |
| 3-Amino-triazole phosphite | | | | | | | | | | | | | | | | 15 | |
| Benzoguanamine phosphite | | | | | | | | | | | | 10 | | | | | |
| Pentaerythritol | | | | | | 0.5 | 1 | 1.5 | 2.5 | 3 | 2 | 2 | 3 | | 3 | 3 | |
| OI (%) | 23 | 25 | 26.5 | 28.5 | 29.5 | 28 | 30 | 31.5 | 31 | 30 | 30.1 | 30.4 | 30 | 24 | 27.3 | 30 | 31 |
| UI 94 TEST thick. 1.6 mm burning time (in s) | | | 0.7 | 0.4 | 0.6 | 0.5 | | 0 | 0.2 | 0 | 0.9 | 0 | 0.2 | | 0 | 0.3 | 0 |
| Classification | V2 | | V2 | V2 | V2 | V2 | | VO | VO | VO | V2 | VO | V2 | V2 | V2 | VO | V2 |
| thick. 3.2 mm burning time (in s) | | 2.2 | 1 | 1.2 | 0.6 | 1.3 | 0.1 | 0.9 | 1.7 | 1.7 | 0.5 | 0.2 | 0.8 | | 0.8 | 1 | 0 |
| Classification | V2 | V2 | V2 | V2 | V2 | V2 | V2 | VO | V2 | V2 | V2 | VO | V2 | V2 | V2 | V2 | V2 |

TABLE II

| Formulation | \multicolumn{10}{c}{EXAMPLES} |
|---|---|---|---|---|---|---|---|---|---|---|
| | 27 | 28 | 29 | 30 | 31 | 32 | 33 | 34 | 35 | 36 |
| Polypropylene - PK 1060 P | 100 | 54.5 | 60 | 65 | 70 | 75 | 65 | | | |
| Polypropylene - 3050 MN | | | | | | | | 100 | 60 | 70 |
| Melamine phosphite | | 35 | 30 | 26.25 | 22.5 | 18.75 | | | 30 | 22.5 |
| Acetoguanamine phosphite | | | | | | | 26.25 | | | |
| Pentaerythritol | | 10.5 | 10 | 8.75 | 7.5 | 6.25 | 8.75 | | 10 | 7.5 |
| OI (%) | 17.3 | 40.5 | 38 | 35 | 31.5 | 30 | 32 | 17.5 | 38.5 | 33.7 |
| Classification in the UL 94 test: | | | | | | | | | | |
| 0.8 mm thickness | | VO | | | | | | | VO | |
| 1.6 mm thickness | | VO | VO | VI | VI | NC | | | VO | |
| 3.2 mm thickness | NC | VO | VO | VO | VO | VI | VO | NC | VO | VO |

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A phosphorous acid salt of formula (I) or (II):

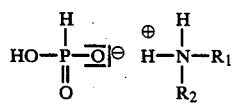

(I)

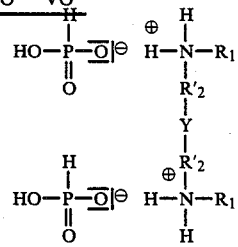

(II)

in which:

$R_1$ is a hydrogen atom, an unsubstituted aliphatic hydrocarbon radical containing from 1 to 6 carbon atoms, a cycloaliphatic radical or a phenyl radical, or one of said radicals substituted by at least one halogen atom or amino group;

$R_2$ is an s-triazine, 1,2,4-triazolyl, benzimidazolyl, heptazine, or 1,3-diazine or is identical to $R_1$;

$R_1$ and $R_2$ together form a divalent group consisting of two said radicals connected by an $\geq$NH residue, —S—, or a methylene residue, or the two radicals $R_1$ in (II) together form a divalent radical;

$R'_2$ is a triazine; and

Y is a group selected from

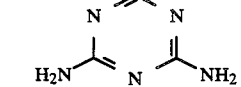, —NH(CH$_2$)$_n$—NH— with n from 2 to 6,

—NH(CH$_2$)$_2$—N(H)—(CH$_2$)$_2$—NH, or

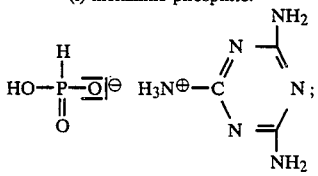

or a single bond.

2. A product of formula (I) of claim 1, wherein RI is a hydrogen atom and R$_2$ is an s-triazine, 1,2,4-triazolyl, benzimidazolyl, heptazine, or 1,3-diazine.

3. A product of claim 2, selected from:

(i) melamine phosphite:

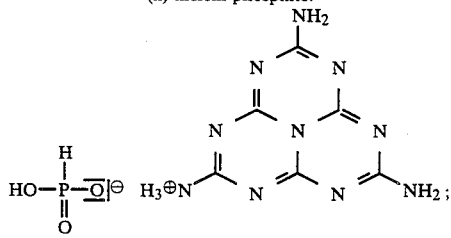

(ii) melem phosphite:

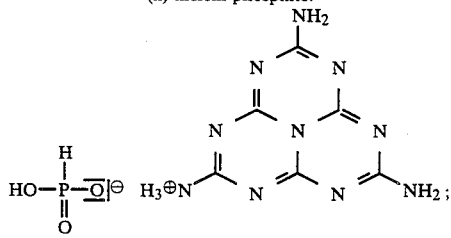

(iii) benzoguanamine phosphite:

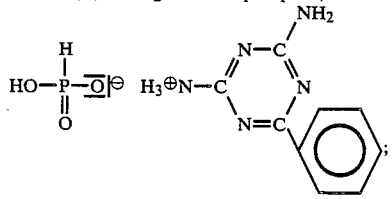

(iv) acetoguanamine phosphite:

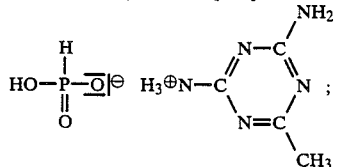

(v) 3-amino-1,2,4-triazole phosphite:

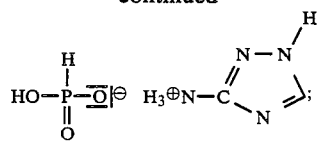

(vi) 4-amino-1,2,4-triazole phosphite:

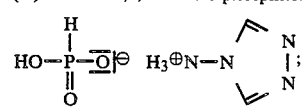

(vii) guanazole phosphite:

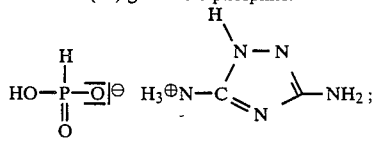

or (viii) benzimidazole phosphite:

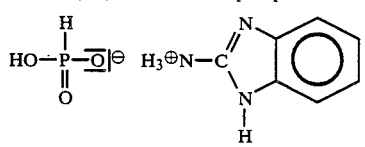

4. A product of formula (I) of claim 1, wherein R$_1$ and R$_2$ are the same and each is a C$_1$ to C$_4$ aliphatic radical or each is a C$_1$ to C$_4$ aliphatic radical substituted by at least one halogen atom or amino group, or R$_1$ and R$_2$ together form a divalent group consisting of two said radicals connected by an >NH residue, a methylene residue, or —S—.

5. The product of claim 4, wherein R$_1$ and R$_2$ are such that a piperazine or piperidine structure is present, and is selected from:

(i) piperazine phosphite:

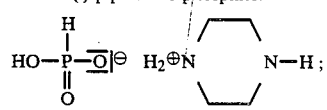

or (ii) piperidine phosphite:

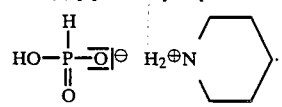

6. A product of formula (II) of claim 1, wherein R$_1$ is a hydrogen and R$_2$ is a radical of triazine structure or is also substituted by at least one amino group, halogen atom or an aliphatic radical containing up to 10 carbon atoms, and the product has the general formula:

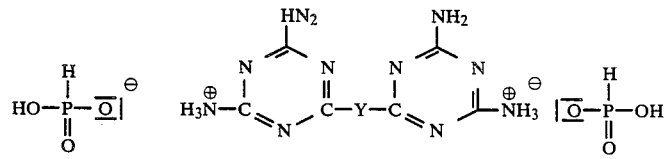

wherein Y is a group as set forth in claim 1.

7. The product of claim 6, selected from:

(i) melam diphosphite:

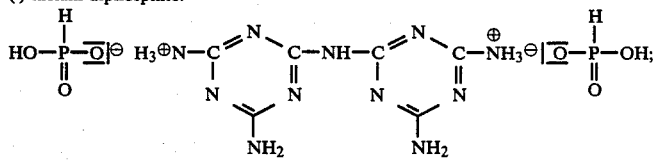

(ii) ethylenedimelamine diphosphite:

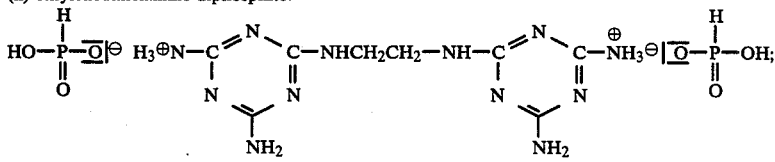

or (iii) diethylenetrimelamine diphosphite:

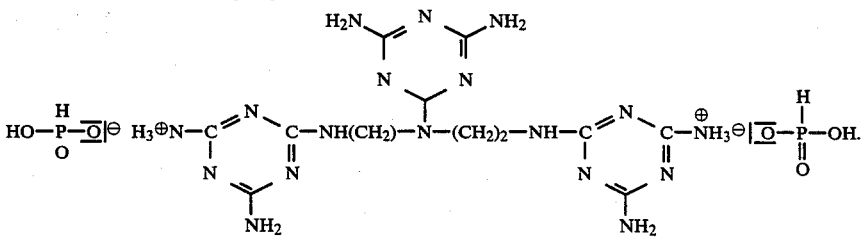

8. A product of formula (II) of claim 1, wherein the two radicals $R_1$ together form a divalent group consisting of two aliphatic residues containing 1 to 2 carbon atoms linked by a single bond, Y is a single bond, and the product is:

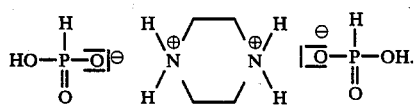

9. The process of fireproofing a plastic comprising adding thereto, in an amount sufficient to fireproof said plastic, a phosphorous acid salt of formula (I) or (II):

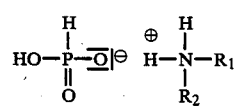 (I)

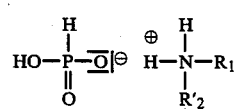 (II)

in which:

$R_1$ is a hydrogen atom, an unsubstituted aliphatic hydrocarbon radical containing from 1 to 6 carbon atoms, a cycloaliphatic radical or a phenyl radical or one of said radicals substituted by at least one halogen atom or amino group;

$R_2$ is a s-triazine, 1,2,4-triazolyl, benzimidazolyl, heptazine, or 1,3-diazine or is identical to $R_1$;

$R_1$ and $R_2$ together form a divalent group consisting of two said radicals connected by an >NH residue, —S—, or a methylene residue, or the two radicals $R_1$ in (II) together form a divalent radical;

$R'_2$ is a triazine; and

Y is a group selected from $$-\underset{H}{N}-,\ -NH(CH_2)_n-NH-\text{ with n from 2 to 6,}$$

$$-NH(CH_2)_2-\underset{H}{N}-(CH_2)_2-NH-,\text{ or}$$

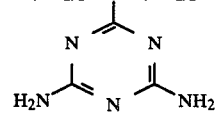

or a single bond.

10. The process of claim 9, wherein melamine phosphite is the product employed.

11. The process of claim 9, wherein the plastic is a polyamide and 1 to 20% by weight of phosphites relative to the fireproofed polyamide is added to said polyamide.

12. The process of claim 9, wherein the plastic is a polyolefin and 10 to 60% by weight of phosphites relative to the fireproofed polyolefin is added to said polyolefin.

13. The process of claim 9, wherein the phosphite is employed in combination with at least one polyhydroxylated compound in an amount sufficient, in combination with the phosphite, to give the desired degree of fireproofing.

14. The process of claim 13, wherein said polyhydroxylated compound is pentaerythritol.

15. The process of claim 13 or 14, wherein 0.2 to 10% by weight of polyhydroxylated compounds relative to the fireproofed polyamide is added to said polyamide.

16. The process of claim 13 or 14, wherein the polyhydroxylated compound is advantageously employed in the polyolefins in such proportion that the molar ratio amine phosphite/hydroxylated compound is between 1 and 7.

17. The process of claim 13 or 14, wherein the quantity of amine phosphite plus polyhydroxylated compound is advantageously between 20 and 60% by weight relative to the fireproofed polyolefins.

18. A fireproofed plastic comprising a plastic containing, in an amount sufficient to fireproof said plastic, a phosphorous acid salt of formula (I) or (II):

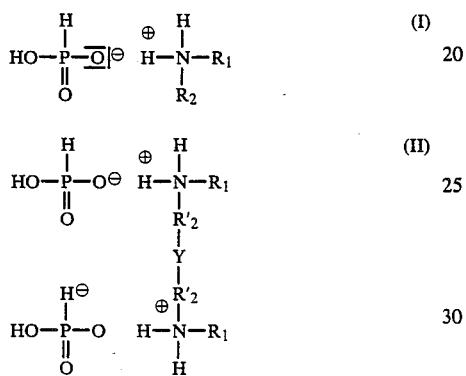

in which:

$R_1$ is a hydrogen atom, an unsubstituted aliphatic hydrocarbon radical containing from 1 to 6 carbon atoms, a cycloaliphatic radical or a phenyl radical or one of said radicals substituted by at least one halogen atom or amino group;

$R_2$ is a s-triazine, 1,2,4-triazolyl, benzimidazolyl, heptazine, or 1, 3-diazine or is identical to $R_1$;

$R_1$ and $R_2$ together form a divalent group consisting of two said radicals connected by an °NH residue, —S—, or a methylene residue, or the two radicals $R_1$ in (II) together form a divalent radical;

$R'_2$ is a triazine; and

Y is a group selected from

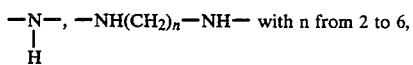

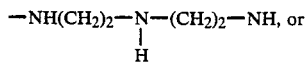

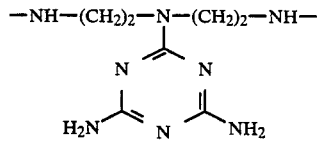

or a single bond.

19. The fireproofed plastic of claim 1 plastic is selected from a polyamide or a polyolefin.

20. The fireproofed plastic of claim 18 or 19, wherein said product is present in an amount of about 1 to 20% by weight based on the weight of a fireproofed polyamide and about 10 to 60% by weight based on a fireproofed polyolefin.

21. The fireproofed plastic of claim 18 or 19 also including at least one polyhydroxylated compound in an amount sufficient, in combination with said phosphorous acid salt, to give the desired degree of fireproofing.

* * * * *

UNITED STATES PATENT AND TRADEMARK OFFICE
CERTIFICATE OF CORRECTION

PATENT NO. : 4,879,327

DATED : November 7, 1989

INVENTOR(S) : Poisson, et al

It is certified that error appears in the above-identified patent and that said Letters Patent is hereby corrected as shown below:

Column 2, line 18, "DETAILED DESCRIPTION" should be centered on line 17.

Column 8, line 44, after "2" and before "1" insert -- : --, line 50, after fireproofing." insert a new paragraph, line 54, after "35%." insert a new paragraph.

Column 10, line 10, insert -- Melamine Phosphite --, line 22, after "condenser." insert a new paragraph, line 54, insert -- Yield: 82%--

Column 11, line 64, insert -- Benzoquanamine phosphite --, line 7, delete -- Benzoquanamine phosphite --, line 12, after "introduced." insert a new paragraph, line 14, after "filtered." insert a new paragraph.

line 69, should read "Yield: 77.82%."

Column 13, line 47, after "minutes." insert a new paragraph.

Column 14, line 16, after "minutes." insert a new paragraph;

line 17 after "C." insert a new paragraph;

Column 15, line 7, after "Company)" insert a -- . -- (period) and insert a new paragraph;

line 40, after "water." insert a new paragraph;

line 50, after "pentaerythritol." insert a new paragraph;

line 63, delete "4hydroxy-phenylpropionyl" and insert -- 4-hydroxy-phenylpropionyl --.

UNITED STATES PATENT AND TRADEMARK OFFICE
CERTIFICATE OF CORRECTION

PATENT NO. : 4,879,327                                    Page 2 of 2
DATED     : November 7, 1989
INVENTOR(S) : Poisson, et al It is certified that error appears in the above-identified patent and that said Letters Patent is hereby corrected as shown below:

Col. 19, line 15, "RI" should be --$R_1$--

Column 20, line 55, after "hydrogen" insert -- atom --.
Column 24, line 6, delete "°" and insert -- > --.
           line 26, "claim 1" should read --claim 18, wherein said --.

Signed and Sealed this

Twenty-sixth Day of February, 1991

Attest:

HARRY F. MANBECK, JR.

Attesting Officer                Commissioner of Patents and Trademarks